(12) United States Patent
Saha (10) Patent No.: US 10,674,741 B1
(45) Date of Patent: Jun. 9, 2020

(54) TEA BREWER

(71) Applicant: Pamela Saha, Seattle, WA (US)

(72) Inventor: Pamela Saha, Seattle, WA (US)

( * ) Notice: Subject to any disclaimer, the term of this patent is extended or adjusted under 35 U.S.C. 154(b) by 483 days.

(21) Appl. No.: 15/617,039

(22) Filed: Jun. 8, 2017

Related U.S. Application Data

(60) Provisional application No. 62/347,269, filed on Jun. 8, 2016.

(51) Int. Cl.
| *A23F 3/18* | (2006.01) |
| *A61L 2/18* | (2006.01) |
| *A61L 2/24* | (2006.01) |
| *A23F 3/14* | (2006.01) |
| *A23F 3/00* | (2006.01) |

(52) U.S. Cl.
CPC .............. *A23F 3/18* (2013.01); *A23F 3/14* (2013.01); *A61L 2/18* (2013.01); *A61L 2/24* (2013.01); *A23F 3/00* (2013.01); *A61L 2202/14* (2013.01)

(58) Field of Classification Search
CPC ..... A47G 19/16; A47G 21/183; A47J 19/005; A47J 31/005; A47J 31/20; A47J 43/27; A47J 31/02; A47J 31/06; A47J 31/0615; A47J 31/0636
USPC .................. 99/281, 279, 300, 319
See application file for complete search history.

(56) References Cited

U.S. PATENT DOCUMENTS

| 2,562,433 | A | * | 7/1951 | Moore | .................... A47J 31/20 99/319 |
| 7,591,219 | B2 | | 9/2009 | Saha | |
| 7,849,785 | B1 | | 12/2010 | Saha | |
| 8,495,951 | B2 | | 7/2013 | Saha | |
| 8,701,550 | B2 | | 4/2014 | Teng | |
| 2013/0279287 | A1 | * | 10/2013 | Cerasani | ............ B65D 47/0885 366/130 |
| 2014/0242240 | A1 | * | 8/2014 | Billadeau | .............. A47J 31/005 426/435 |

OTHER PUBLICATIONS

Jokari Tea Infuser; First advertised 2011.

* cited by examiner

*Primary Examiner* — Dana Ross
*Assistant Examiner* — Joe E Mills, Jr.
(74) *Attorney, Agent, or Firm* — James Creighton Wray (57) ABSTRACT

Brewing apparatus and methods have a body, a movable member in the body, concentric relatively sliding tubes or a tube and a rod. A first tube or rod is attached to the body. A second tube or rod is attached to the movable member. A substance is placed in the body. The body is lifted and lowered into a brewing vessel using the first tube. After brewing, the second tube lowers the movable member to compress the substance. The first member lifts the body and places it on a caddy stand. Cooperating projections, depressions, detents and receivers align and snap the body on the caddy stand with the body and tubes held vertically.

19 Claims, 10 Drawing Sheets

TEA BREWER

This application claims the benefit of U.S. Provisional Application No. 62/347,269 filed Jun. 8, 2016, which is hereby incorporated by reference in its entirety as if fully set forth herein.

BACKGROUND OF THE INVENTION

Tea has always been popular and recently has become more popular. One difficulty remains in how neatly to remove tea sachets or bags or loose tea from brewed tea.

Another problem remains in how to conveniently remove brewed tea from the wet tea sachets, bags and soaked tea leaves. The problems are exacerbated by the staining capability of the liquid concentrate that exudes from the wet sachets, bags or loose tea. The same problems result when using bags, sachets or loose particles to brew other beverages.

Needs exist for improved beverage brewers.

SUMMARY OF THE INVENTION

The present invention solves the problems associated with the enjoying of tea and hot beverages. Tea is an example that will be used. The brewed tea is substantially removed from the soaked tea sachets, bags and loose leaves. Any final drips of the concentrated fluids are received within a saucer on which the tea brewer fits. Strong tea lovers may want to raise the saucers and brewers and tip the strong concentrates from the saucers into their tea cups.

A brewer has a cup, a lid, a movable element and tubes extending upward from the lid. The cup has a top, walls and a base configured for holding a substance for brewing. Holes in the at least one of the walls and the base flow a liquid through substance within the cup. The lid has a top and a bottom and an opening in the top of the lid, A first connector on the cup and a second complementary connector on the lid join the cup and the lid. Separating the lid from the cup, placing the substance for brewing in the cup and joining the lid and the cup prepare for lowering the cup into a brewing vessel. Later, before raising the lid and the cup together from a beverage container, a movable element compresses the substance within the brewer.

A tube extends outward from the top of the lid, and an elongated connector extends through the tube from an interior of the brewer. The tube and the elongated connector are configured for lowering the brewer into a brewing vessel, moving the movable element within the brewer, expressing liquid from the substance within the brewer and lifting the brewer from the vessel.

A caddy holds the brewer upright. The caddy has a saucer-like shape with a base and raised side edges and holds the brewer to collect drips after the brewer is lifted from a brewing vessel. A caddy projection or depression at or near a middle of the caddy cooperates with a complementary cup depression or projection at or near a middle of the base of the cup. The complementary depression and projection are configured for centering and holding the brewer upright at or near a center of the caddy.

A projection has one or more outward detent. A depression has one or more complementary inward extending detent receivers for snapping the holder and caddy stand together and holding the brewer in place on the caddy.

In one example, the tube extending outward from the top of the lid is a translatable outer tube configured for moving through an opening at the top of the lid. The movable element is connected within the brewer to an inner end of the translatable outer tube. The elongated connector is a rigid rod or an inner tube having a first inner end connected to the base of the cup. The top of the rod or inner tube is grasped to move the brewer into and out of the beverage container and onto a caddy.

In one form, the elongated connector is an inner tube having a first inner end connected to the base of the cup and configured to move the brewer into and out of the beverage container and onto a caddy. The inner tube has one or more openings adjacent the first inner end for withdrawing fluid from or adding fluid to the brewer.

In one form, the holes are microtubular pores.

A cup-shaped filter is provided for insertion in the cup of the brewer for holding the substance within the brewer.

A permeable bag with a drawstring is configured for holding the substance within the brewer, In one embodiment, a brewer body has a top, a bottom and ribs extending between the top and the bottom, leaving spaces between the ribs. A hollow outer tube extends upward from the top, and an inner tube or rod extends through the outer tube. A movable member mounted between the ribs and between the top and the bottom of the body is attached to a lower end of the inner tube or rod. The outer tube is attached to the body for raising and lowering the brewer. The body, the movable member and the outer tube and the inner tube or rod are configured for raising the inner member, inserting a permeable container of a substance to be brewed and lowering the body into a vessel for brewing. Later, pressing the inner member upon the permeable container compresses the substance. Withdrawing the body from the vessel, raising the movable member within the body and removing the permeable container from the body readies the body for snapping onto a caddy stand and collecting drips. The permeable container comprises a permeable bag with a drawstring for holding the substance to be brewed.

A method includes providing a body, providing a movable member of the body, providing an outer tube, providing an inner tube or rod, connecting a lower end of a first one of the outer tube and the inner tube or rod to the movable member and connecting a lower end of a second one of the outer tube and the inner tube or rod to the body.

After inserting a substance for brewing into the body, lifting the body with the second one of the outer tube and the inner tube or rod and lowering the body into a brewing vessel with the second one of the outer tube and the inner tube or rod, fluid flows through the body and the substance for brewing within the vessel.

Moving the movable member toward a bottom of the body with the first one of the outer tube and the inner tube or rod while lifting the body out of the brewing vessel with the second one of the outer tube and the inner tube or rod compresses the substance and drains the body to the vessel.

Lowering the body onto the caddy stand is aided with the second one of the outer tube and the inner tube or rod.

Complementary projection and depression on the body and the caddy stand and cooperating complementary detents and receivers on the projection and depression allow snapping the cooperating complementary detents and receivers together, which prevents tipping of the brewer and spilling of collected drips.

These and further and other objects and features of the invention are apparent in the disclosure, which includes the above and ongoing written specification, with the claims and the drawings.

DETAILED DESCRIPTION

As shown in FIGS. 1-4, rod 1 has its bottom attached to porous cup 4. The bottom cup 4 has holes 41 and is cylindrical to hold the tea leaves to be brewed. The tea leaves may be loose or in a sachet or bag. The base 44 of the bottom cup rests against a bottom of a tea cup.

The top sliding upper cup assembly 2 with a long hollow tubular handle 21 has an inverted top cup 22 or disk at a lower end of the tubular handle. The cup 22 squeezes the tea leaves as the hollow handle 21 is moved downward. The tube 21 that slides on the rod is long enough to be grasped by the user. The tubular handle 21 holding the top cup 22 slides through the hole 31 in the top lid 3 that is attached to the bottom cup 4. The bottom cup 4 is the container of the tea leaves. The downward sliding of the handle continues until the top cup 22 reaches and makes contact with the bottom 42 of cup 4 or is held away from the bottom by the compressed tea leaves.

The hole 31 in the top lid 3 fits over the top sliding cup 22 and its tubular handle 21. The top lid 3 is screwed onto the open top of cup 4. The top cup 22 slides along the rod 1. Lower end 11 of rod 1 is attached to the bottom of cylindrical porous bottom 42 cup 4. After placing tea leaves in the lower cup, a lower edge 33 of the lid 3 connects with or fits on a top 43 of the bottom porous cup 4, forming an enclosure 6.

The cylindrically shaped bottom cup 4 is porous and is deeper than the lid 3, which completes an enclosed brewing space for the tea leaves within the bottom cup. The upper cup 22 and hollow handle 21 are held upward by friction or by the volume of tea leaves. After a reasonable time of brewing, the handle is slid downward, causing the upper inner cup to compress the leaves. The entire assembly 10 is raised from the tea cup by lifting the handle 1. The assembly 10 is moved to the saucer caddy.

Figure 1:
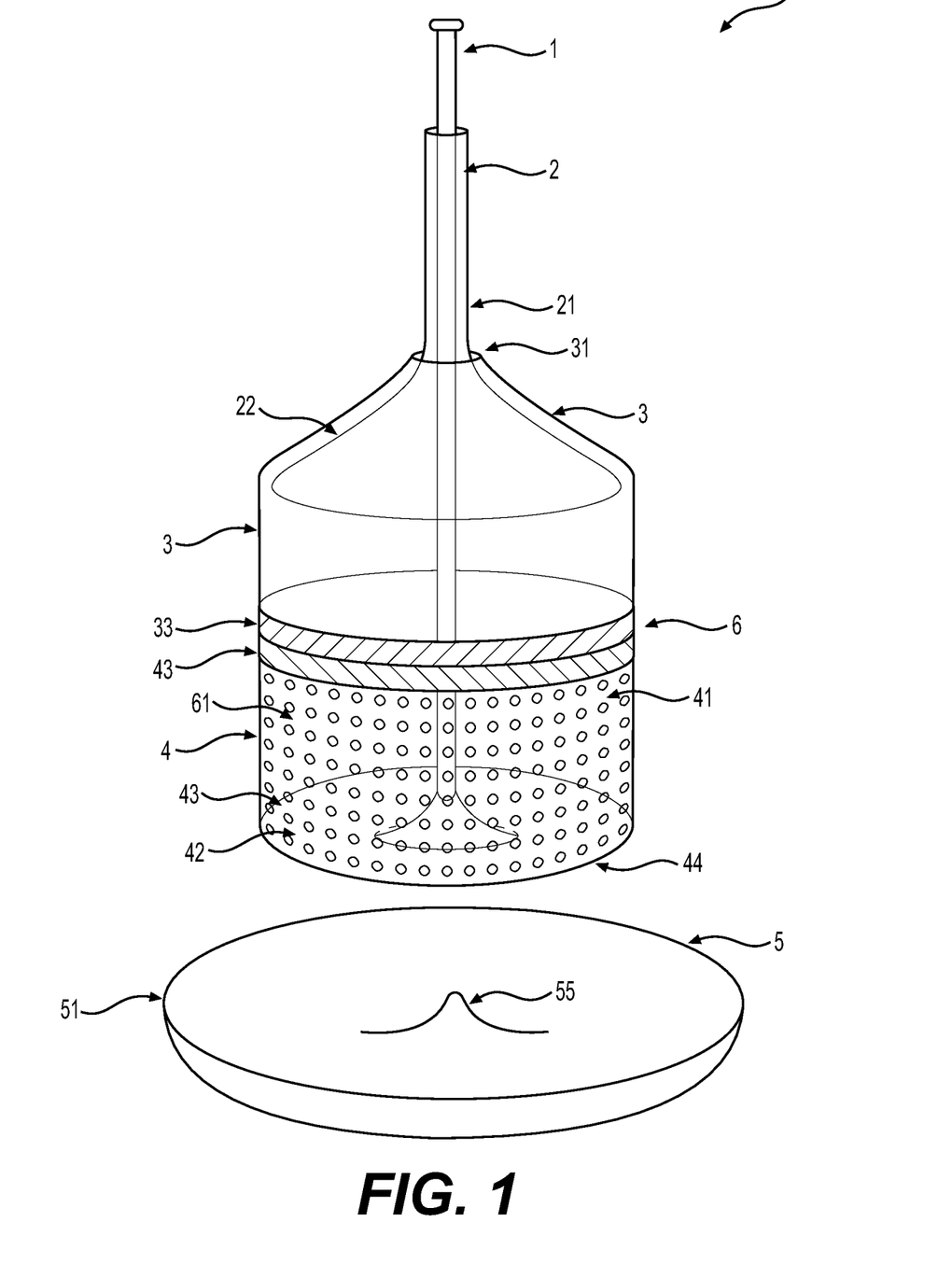
FIG. 1 is a perspective view of a tea brewer of the invention.
Figure 2:
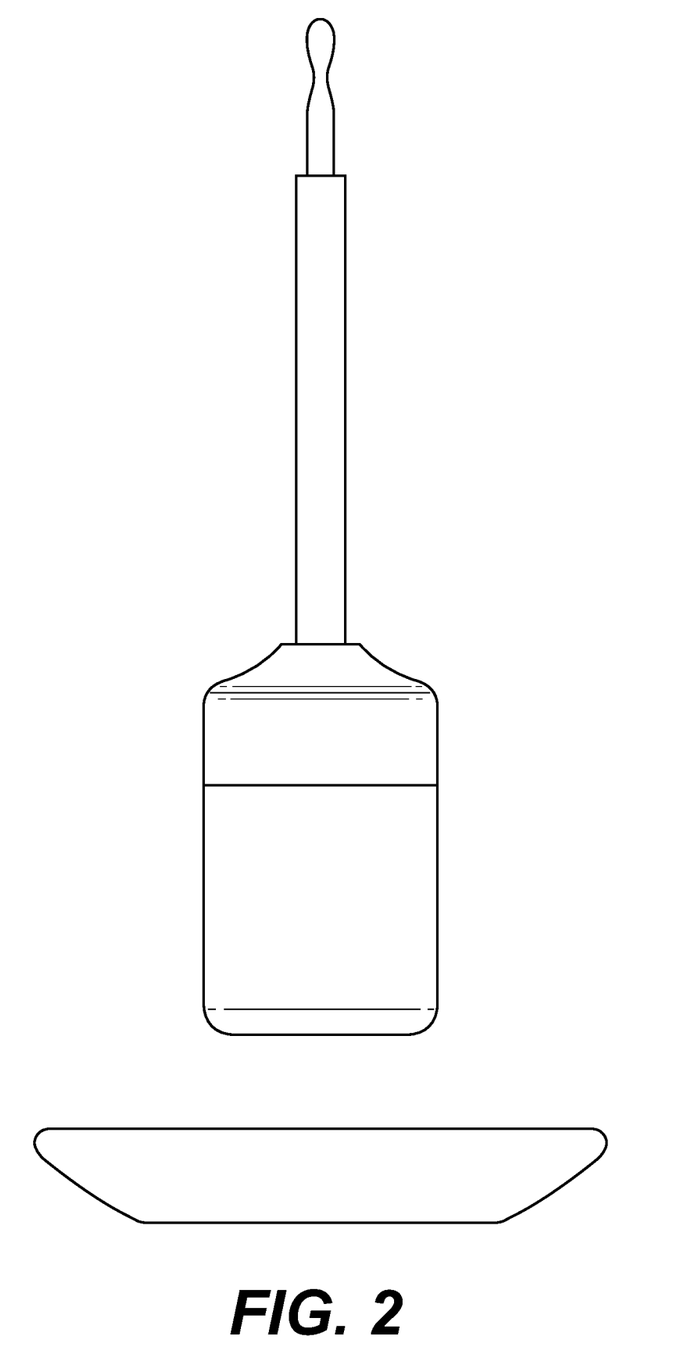
FIG. 2 is a side perspective view of the tea brewer shown in FIG. 1.
Figure 3:
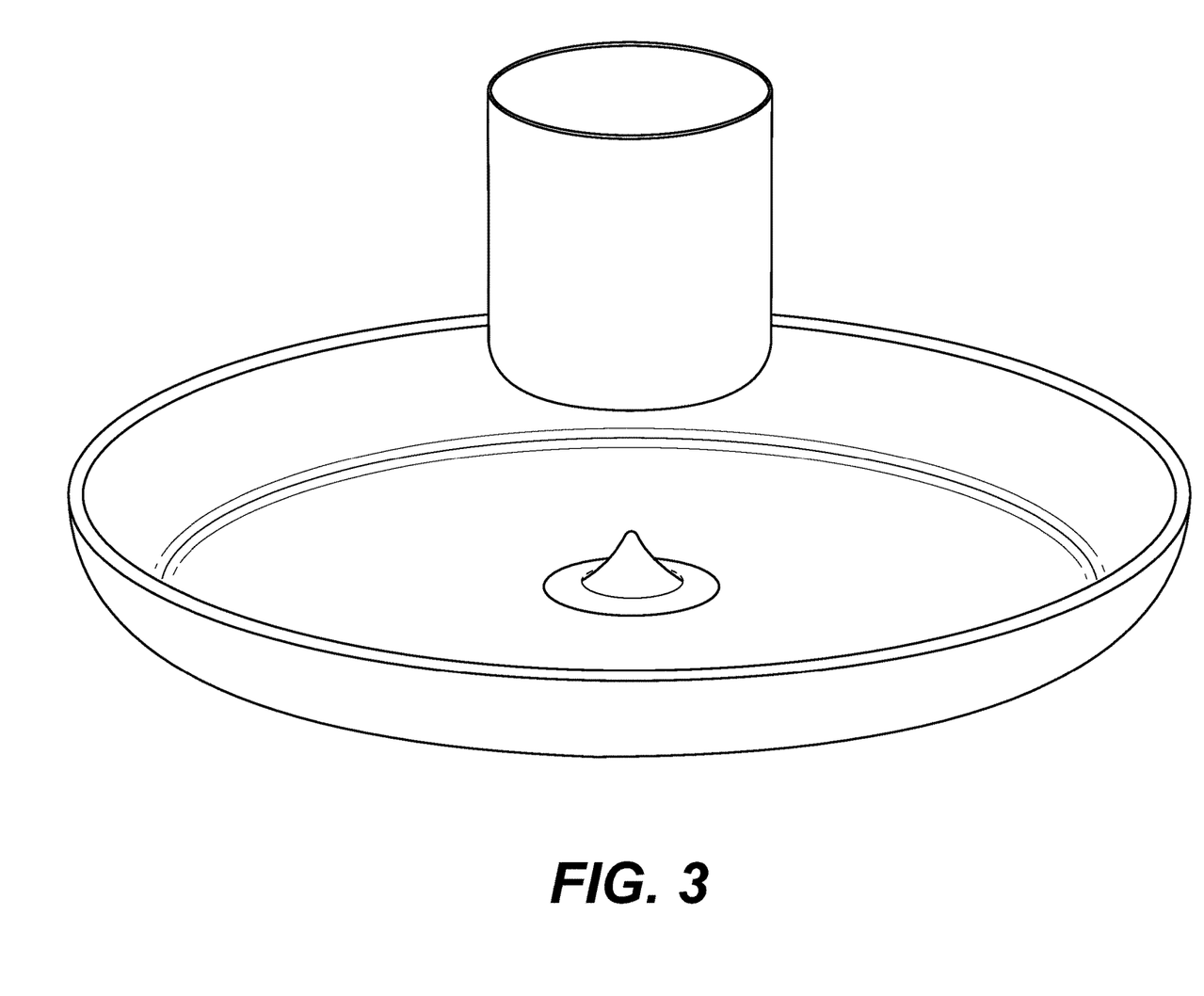
FIG. 3 is a top and side perspective view of the base of the brewer and the saucer which holds and attached to the base shown in FIGS. 1 and 2.
Figure 4:
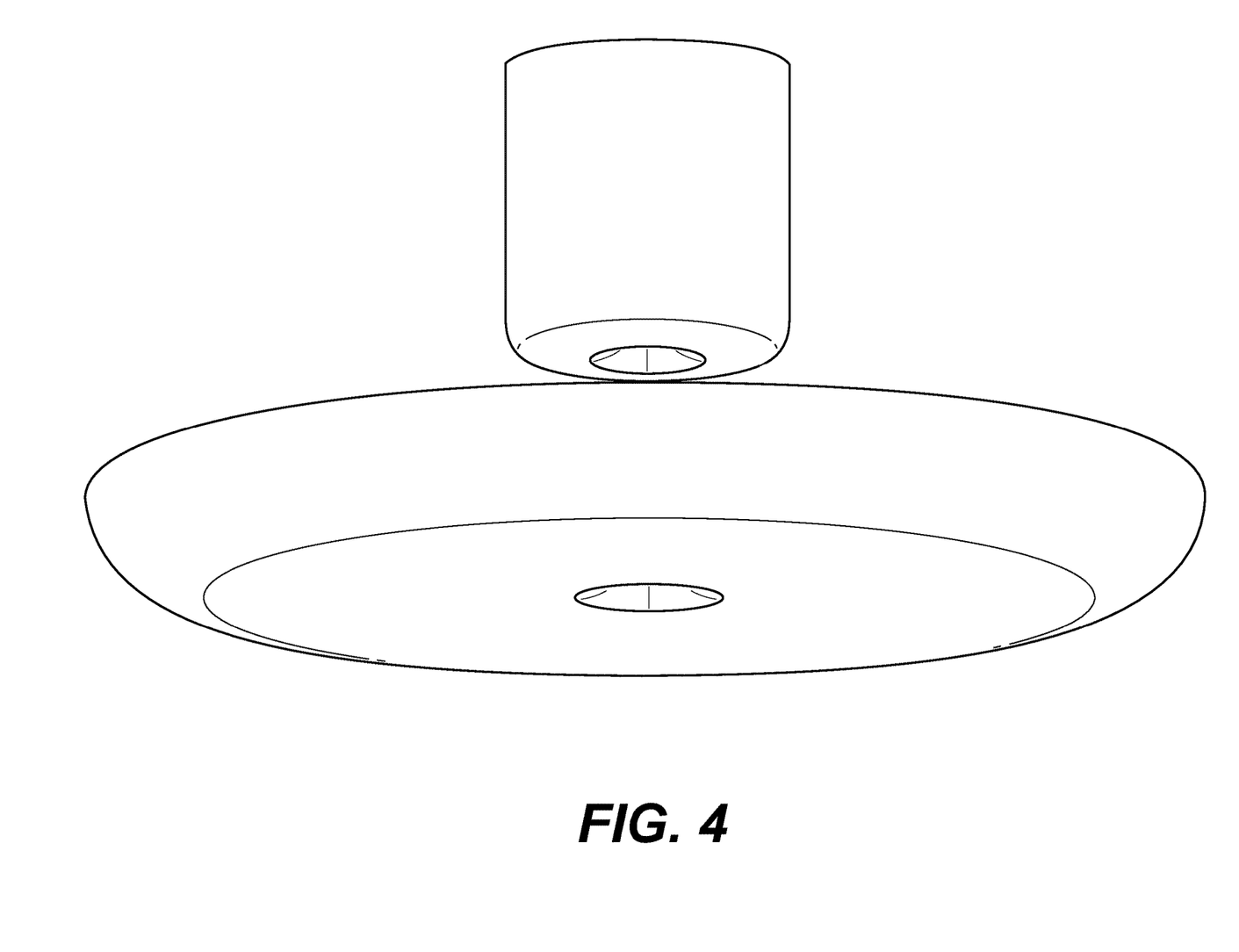
FIG. 4 is a bottom perspective view of the base of the brewer and the saucer which holds and attached to the base shown in FIGS. 1 and 2.

The saucer is a caddy 5 on which base 44 of the bottom cup 4 fits. As a kind of ball/socket or snap-in fixation, the central area of the caddy 5 forms a protrusion 55 to fit a central recessed cavity 45 within the base 44 of the porous bottom cup 4. Three or more lateral outward projections 57 on the protrusion 55 may fit into one or more complementary inward receiver indentations 47 in the recessed cavity 45 within the base 44. Alternatively, three or more receiver indentations may be formed in the protrusion 55 in saucer 5, and complementary radially inward projections may be formed on the recessed cavity 45 in base 44. The receiver indentations may be replaced by a circumferential groove in the recessed cavity of the base to cooperate with projections on the protrusion 55. The receiver indentations may be a groove formed around the protrusion 55 for receiving radially inward projections on the recessed cavity 45 of base 44. This allows the caddy 5 to hold the brewing device 10 standing for reuse. The saucer 51 of the caddy 5 also serves to catch to drippings from the porous bottom cup after using the brewing device 10.

Tea may be sipped through an extended hollow rod 21. The feature of extending the hollow rod to be able to sip tea is optional. Rod 1 can be solid or hollow. As a hollow rod it can be an optimal means of sipping tea over the choice of rod 21. Another option is to make it a pipette sized hollow rod that can serve for sipping as well as facilitating the absorption of liquid into the enclosure 6 which is the brewing chamber. Liquid would rise from the end of hollow rod 1 at the base of the enclosure and through strategically placed openings or holes along the hollow rod 1 that opens into enclosure 6.

Figure 5:
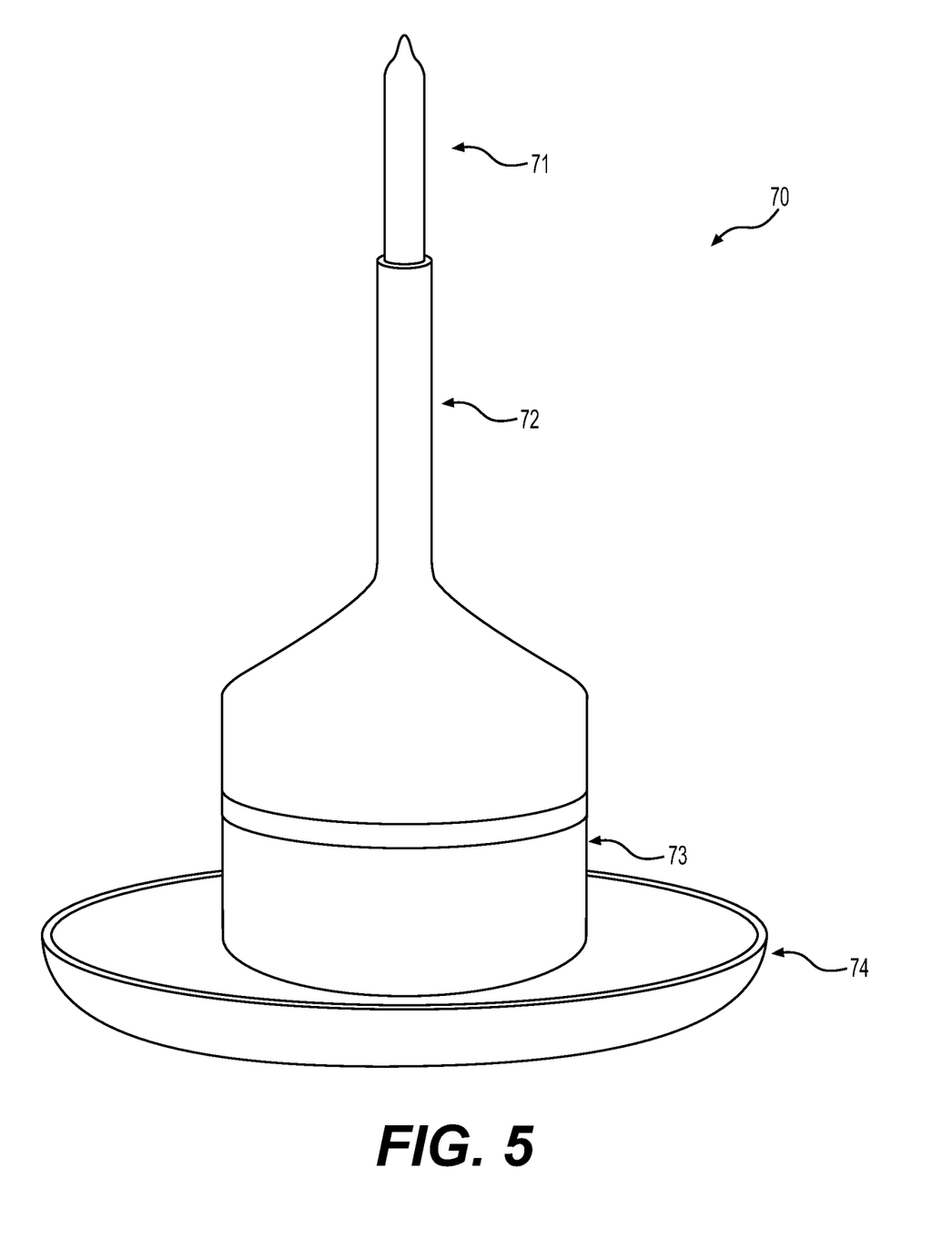
FIG. 5 is a perspective view of another tea brewer of the invention.
Figure 6:
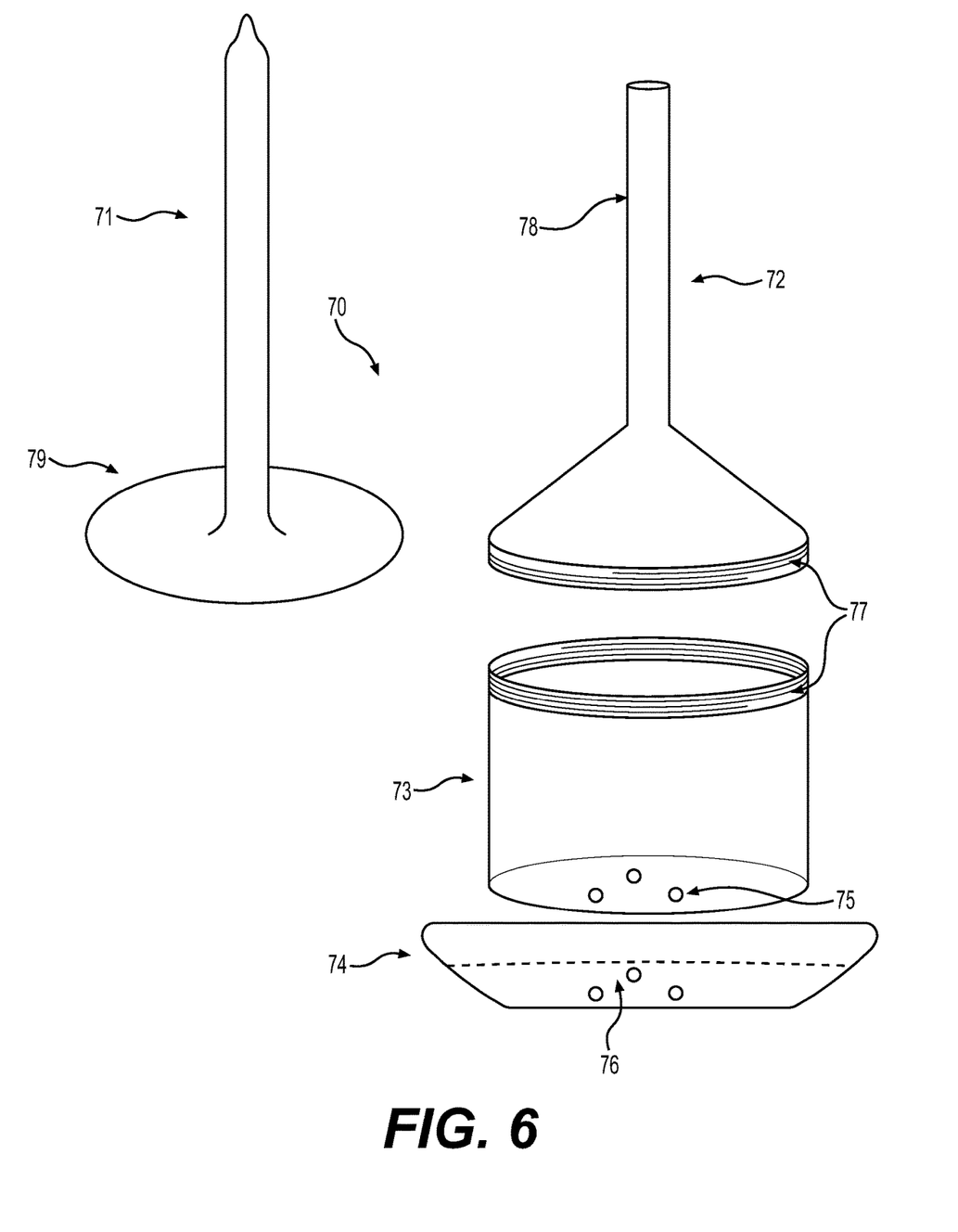
FIG. 6 is an exploded perspective view of parts of the tea brewer shown in FIG. 2.
Figure 7:
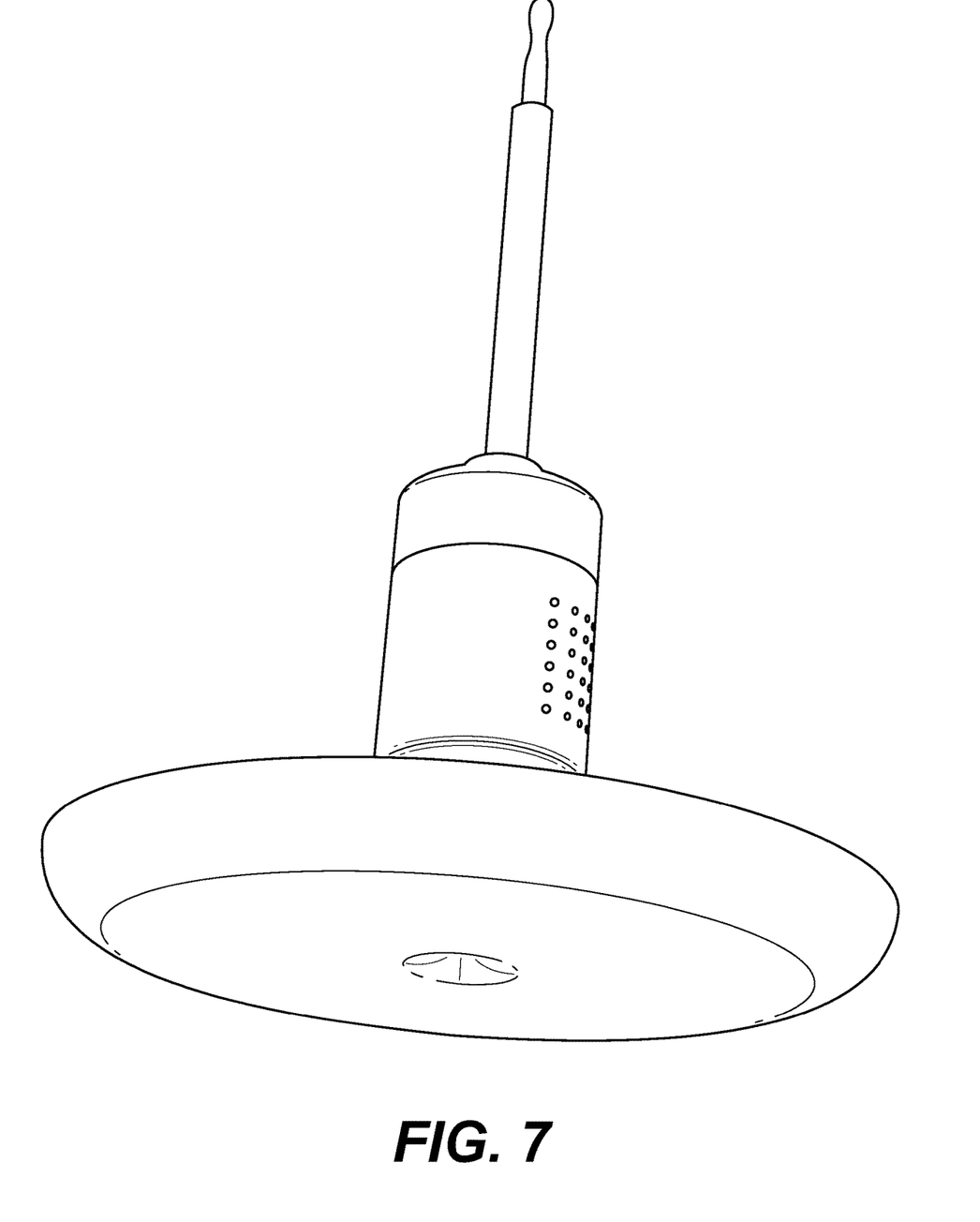
FIG. 7 is a bottom perspective view of the tea brewer shown in FIGS. 2 and 3.

As shown in FIGS. 5, 6 and 7, a tea brewer 70 has a sliding rod 71 that slides through the top tube 78 of cover assembly 72. The tea brewer 70 is placed into and later removed from a tea cup by lifting the outer tube 78. Before lifting out of the tea cup, the inner rod 71 is slid downward to compress the tea and to reduce the fluid remaining in the brewer. The fluid exits through the porous walls of the holder as the brewer 70 is lifted from the tea cup. A conical or flat press plate 79 is connected to a base of rod 71. A base tea holder 73 is connected to the top by complementary quick connectors 77 which may be snaps, bayonet threads or continuous threads. Walls of the tea holder 73 are porous. Saucer caddy 74 holds the brewer 70 after it has been removed from a cup or pot of tea.

Indentations 75 in the base of the holder 73 cooperate with projections 76 in the center of the saucer caddy 74 to center and hold the vertical alignment of the resting brewer. The cooperating indentations and projections 75 and 76 may be reversed and, in some modifications, once co-located the cooperating indentations and projections may be snapped into place with light pressure to hold the vertical alignment of the brewer 70.

Projections 75 may be formed on the base of the tea holder 73 to raise the base of the holder 73 above the caddy saucer 74 so that drips collected in the saucer will not adhere to holder 73 when it is raised from the saucer.

As an example, the tea server shown in FIGS. 1-7 may have a height of less than 7 inches, a cup and lid 2.5 inches tall and 1.5 inches in diameter, and a saucer 3.5 inches in diameter.

The invention allows for a free standing configuration for reuse that also collects drippings while the customer sips the tea. It also allows for an easy and less messy way to put less tea in the device and secure it on the device for use. Still further, it comes apart for effective cleaning of the entire device for reuse and can be made entirely of an inexpensive plastic and is therefore disposable.

FIG. 7 is a bottom view of a saucer attached to the brewer shown in FIGS. 5 and 6.

Figure 8:
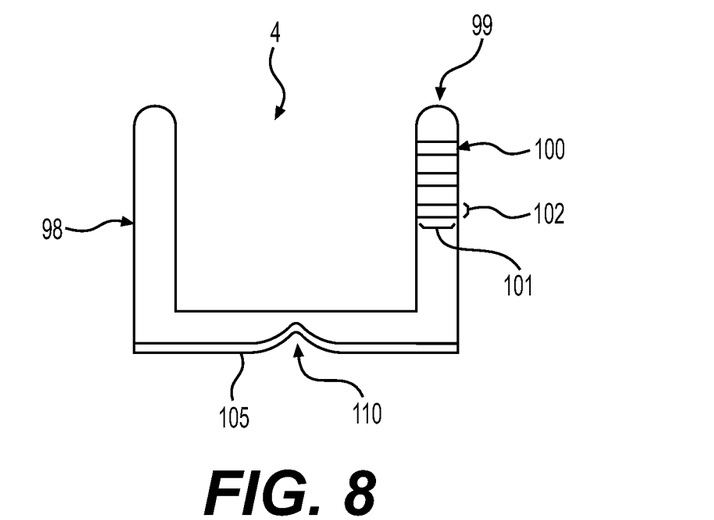
FIG. 8 is a cross-sectional view of a tea brewer bottom cup.

FIG. 8 shows a cross-section 98 of the bottom cup 4 or chamber for containing the tea. Wall 99 of the chamber has a significant thickness. Microtubules 100 through the wall 99 of the chamber draw fluid by capillary action into the chamber holding the tea leaves. These microtubule pores 100 are all over the sides and bottom of the chamber. The invention includes placement of the microtubes 100 only in certain areas of the chamber.

Length 101 of microtubule pores 100 is substantial. Diameter 102 of microtubules 100 is smaller than length 101 of the microtubule pores 100.

Figure 9:
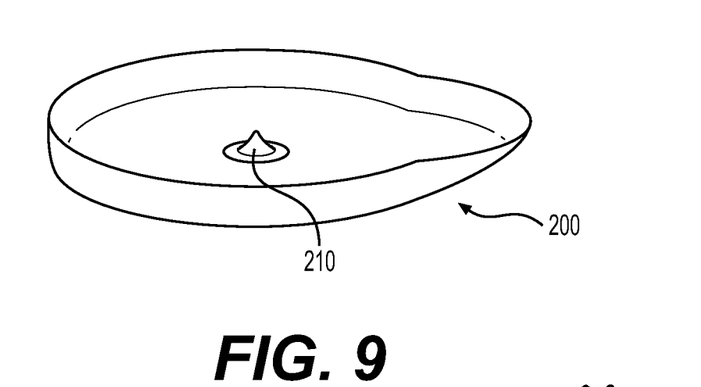
FIG. 9 is a perspective view of the caddy stand with a snap feature in its center for securing the tea brewer.

The bottom 105 of the chamber has a snap feature 110 to connect with a complementary snap feature 210 on the tea caddy stand 200 shown in FIG. 9. An alternative connection feature on the bottom of the chamber may cooperate with an accompanying complementary connection feature on caddy stand 200.

FIG. 9 shows caddy stand 200 that has a pouring spout and a central snap connection feature 210 for cooperating in holding the tea bottom cup 4 snap feature 110 until the two snap features are intentionally separated.

Figure 10:
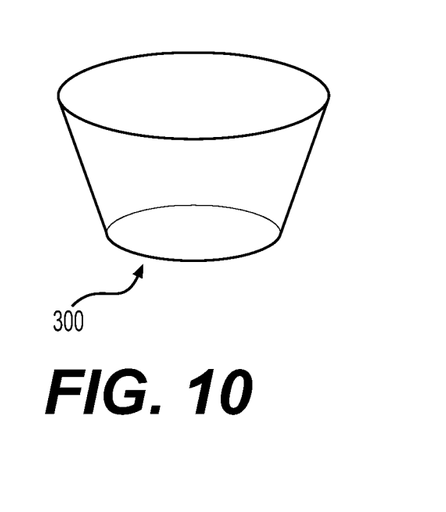
FIG. 10 is a perspective view of a filter.

FIG. 10 shows a cup-shaped filter 300 for holding loose tea leaves in one of the brewers of the invention.

Figure 11:
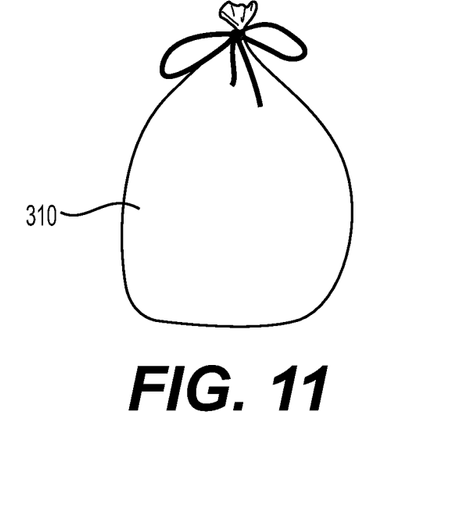
FIG. 11 shows a tea bag with a drawstring.

FIG. 11 shows a reusable tea bag 310 with a drawstring 312 for closing and opening tea bag 310.

Figure 12:
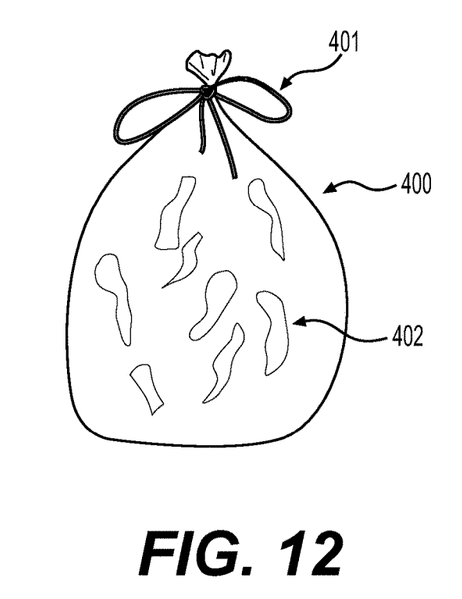
FIG. 12 shows a drawstring tea bag with loose tea inside.

In a form of the invention, such as shown by example in FIG. 12, a tea bag 400 with a pull closure string 401 is used to hold loose tea leaves 402. Tea bag 400 is usable in the tea brewers shown in FIGS. 1-11. The bag is also useful in the tea brewer 410 shown in FIG. 13.

Figure 13:
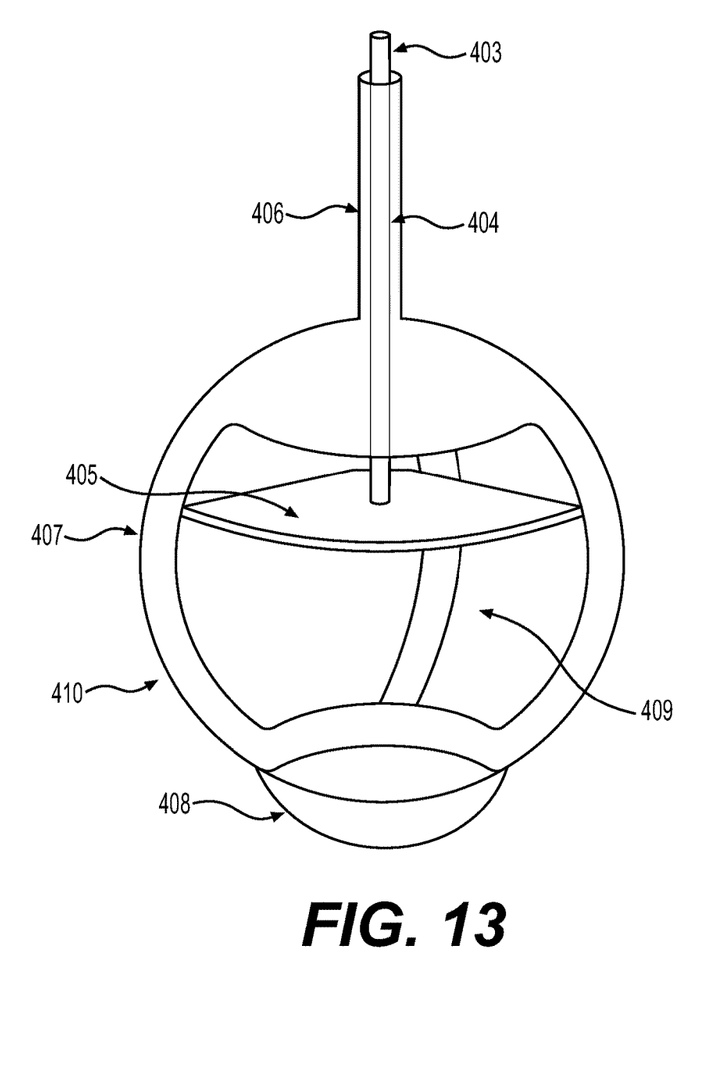
FIG. 13 is a perspective view of an embodiment of the tea brewer.

In the brewer 410 shown in FIG. 13, a rod 403 is slid through tube 406 with a central part 404 having a light holding friction. Rod 403 pushes a plate 405 downward to squeeze a tea bag placed within ribs 407 into a cup 408 at the bottom of central space 409 of the tea brewer 410. The lower cup 408 may be foraminous to allow passage of the liquid tea expressed from the tea bag out of the cup. The cup may have a closed bottom to retain drippings. Cup 408 has a central connection feature for connecting to a complementary connecting feature in a tea caddy, as shown in FIG. 9.

Figure 14:
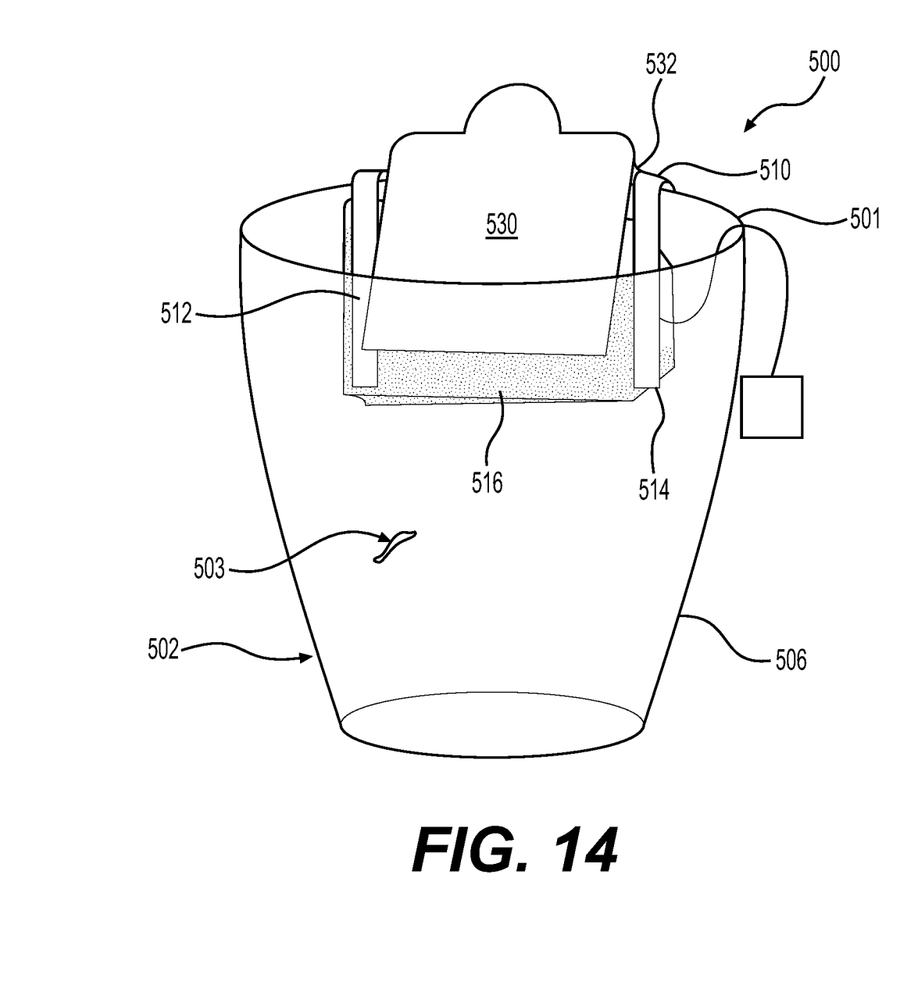
FIG. 14 shows a tea bag in a tea bag holder within a cup.
Figure 15:
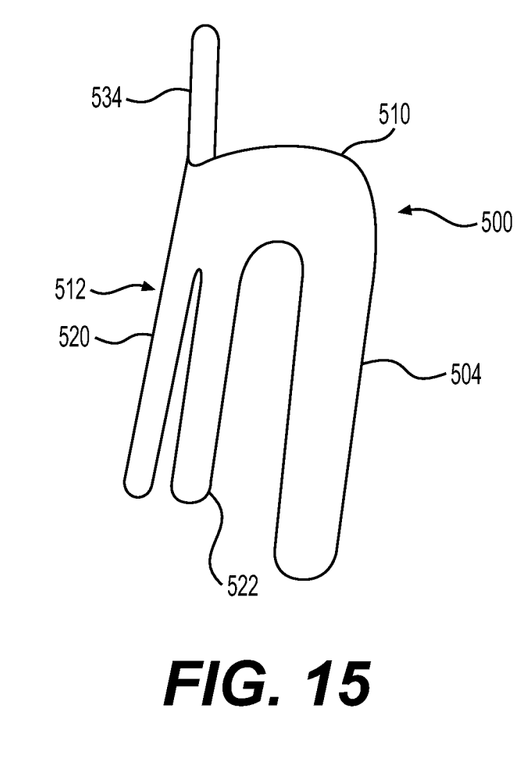
FIG. 15 is a cross-sectional view of the tea bag holder shown in FIG. 11.

FIGS. 14 and 15 show a tea brewer as a tea bag holder 500 held on an upper edged 501 of a cup 502. The tea bag holder 500 has a solid structure 504 that overlies an outside 506 of a cup 502 near its upper edge 501. Curved upper portions 510 of the tea bag holder 500 fit over the upper edge 501 of cup 502. Tea bag holding clips 512 extend downward from the curved upper portion 570 into an interior 503 of the cup.

A paddle 530 is suspended on two hinges 532 connected to the curved upper portions 510. A tea bag 516 is slid upward in the space 518 between two prongs 520,522 of each clip 512. Edges 514 of the tea bag 516 are slid into the cup clips 512 so that when the holder 500 is placed on the cup, the tea bag 516 will be between the paddle 530 and the wall of the cup. An upward extension 534 of the paddle is pressed forward to move the paddle forward toward the cup wall, if it is desired to squeeze the tea bag while the tea is brewing. Upon lifting the holder 500 from the cup after brewing is completed, the extension 530 may be moved forward to squeeze the tea bag 516 against the solid structure 504 of the holder while holding the holder, while holding the holder above the cup.

After squeezing the holder 500, wet tea bag 516 may be placed on a saucer without dripping.

While the invention has been described with reference to specific embodiments, modifications and variations of the invention may be constructed without departing from the scope of the invention, which is defined in the following claims.

I claim:

1. Apparatus comprising
a brewer, further comprising
a cup having a top, walls and a base configured for holding a substance for brewing,
holes in the at least one of the walls and the base for flowing a liquid through substance within the cup,
a lid having a top and a bottom, and an opening in the top of the lid,
first and second complementary connections, the first complementary connection being connected to the cup and the second complementary connection being connected to the lid for joining the cup and the lid, the complementary connections being configured for separating the lid from the cup, placing the substance for brewing in the cup and joining the lid and the cup before lowering the cup into a beverage container and later raising the lid and the cup together from a beverage container,
a conical or flat press plate for compressing a substance within the brewer,
a tube extending outward from the top of the lid, and an elongated connector extending through the tube from an interior of the brewer,
wherein the tube and the elongated connector are configured for lowering the brewer into a beverage container, moving the conical or flat press plate within the brewer and for expressing liquid from the substance within the brewer and for lifting the brewer from the beverage container.

2. The apparatus of claim 1, further comprising a caddy for holding the brewer, the caddy further comprising a saucer-like shape with a base and raised side edges configured for holding the brewer after the brewer is lifted from a beverage container, and a caddy projection or depression at or near a middle of the caddy.

3. The apparatus of claim 2, wherein the brewer further has a complementary cup depression or projection at or near a middle of the base of the cup, the caddy projection or depression and the complementary cup depression or projection configured for centering and holding the brewer upright at or near a center of the caddy.

4. The apparatus of claim 3, wherein the caddy has the caddy projection and the brewer has the cup depression extending upward from the base into the cup for receiving the caddy projection.

5. The apparatus of claim 3, wherein each projection further comprises one or more outward detent extensions, and wherein the depression has one or more complementary inward extending detent receivers for receiving the one or more outward detent extensions, container configured for holding the brewer in place on the caddy.

6. The apparatus of claim 3, wherein each depression has one or more outward detent extensions, and wherein each projection has one or more complementary inward extending receivers for receiving the one or more outward detent extensions, and wherein the detent extensions and the detent receivers are configured for holding the brewer in place on the caddy.

7. The apparatus of claim 1, wherein the tube extending outward from the top of the lid is a translatable outer tube configured for moving through an opening at the top of the lid, wherein the conical or flat press plate is connected within the brewer to an inner end of the translatable outer tube, and wherein the elongated connector is a rigid rod or an inner tube having a first inner end connected to the base of the cup and being configured to move the brewer into and out of the beverage container and onto a caddy.

8. The apparatus of claim 1, wherein the tube extending outward from the top of the lid is a translatable outer tube configured for moving through an opening at the top of the lid, wherein the conical or flat press plate is connected to an inner end of the translatable outer tube within the brewer, and wherein the elongated connector is an inner tube having a first inner end connected to the base of the cup and configured to move the brewer into and out of the beverage container and onto a caddy, and wherein the inner tube has one or more openings adjacent the first inner end configured for withdrawing fluid from or adding fluid to the brewer.

9. The apparatus of claim 1, wherein the holes are microtubular pores.

10. The apparatus of claim 2, wherein the base of the cup and the caddy have complementary snap features.

11. The apparatus of claim 1, further comprising a cup-shaped filter configured for insertion in the cup of the brewer for holding the substance within the brewer.

12. The apparatus of claim 1, further comprising a permeable bag with a drawstring configured for holding the substance within the brewer.

13. Apparatus comprising:
a brewer, further comprising:
a body having a top, a bottom and ribs extending between the top and the bottom leaving spaces between the ribs,
a hollow outer tube extending upward from the top and an inner tube or rod extending through the outer tube, the outer tube and the inner tube or rod having upper and lower ends,
a plate within a space between the ribs and between the top and the bottom of the body and attached to a lower end of a first one of the outer tube and the inner tube or rod, and wherein a second one of the outer tube and the inner tube or rod is attached to the body for raising and lowering the brewer,
wherein the body, the plate and the outer tube and the inner tube or rod are configured for raising the plate, inserting a permeable container of a substance to be brewed, lowering the body into a vessel for brewing, pressing the inner member upon the permeable container, withdrawing the body from the vessel, raising plate within the body and removing the permeable container from the body.

14. The apparatus of claim 13, wherein the permeable container comprises a permeable bag with a drawstring for holding the substance to be brewed.

15. A method comprising:
providing a body,
providing a conical or flat press plate of the body,
providing an outer tube,
providing an inner tube or rod,
connecting a lower end of a first one of the outer tube and the inner tube or rod to the conical or flat press plate,
connecting a lower end of a second one of the outer tube and the inner tube or rod to the body,
inserting a substance for brewing into the body,
lifting the body with the second one of the outer tube and the inner tube or rod,
lowering the body into a brewing vessel with the second one of the outer tube and the inner tube or rod,
flowing fluid through the body and the substance for brewing within the vessel,
moving the conical or flat press plate toward a bottom of the body with the first one of the outer tube and the inner tube or rod, and
lifting the body out of the brewing vessel with the second one of the outer tube and the inner tube or rod.

16. The method of claim 15, further comprising providing a caddy stand and lowering the body onto the caddy stand with the second one of the outer tube and the inner tube or rod.

17. The method of claim 16, providing cooperating complementary projection and depression on the body and the caddy stand.

18. The method of claim 17, further comprising providing cooperating complementary detents and receivers on the projection and depression.

19. The method of claim 18, further comprising snapping the cooperating complementary detents and receivers together.

* * * * *